United States Patent
Haking et al.

(10) Patent No.: US 6,563,112 B1
(45) Date of Patent: May 13, 2003

(54) METHOD FOR ENHANCING THE CONTRAST FOR A TRANSMISSION ELECTRON MICROSCOPE

(75) Inventors: Ansgar Haking, Eppelheim (DE); Helmut Tröster, Mannheim (DE); Karsten Richter, Ketsch (DE); Michael Trendelenburg, Im Insenbühl (DE)

(73) Assignee: Deutsches Krebsforschungszentrum Stiftung Des Öffentlichen Rechts, Heidelberg (DE)

( * ) Notice: Subject to any disclaimer, the term of this patent is extended or adjusted under 35 U.S.C. 154(b) by 0 days.

(21) Appl. No.: 09/623,933
(22) PCT Filed: Mar. 12, 1999
(86) PCT No.: PCT/DE99/00727
§ 371 (c)(1), (2), (4) Date: Oct. 27, 2000
(87) PCT Pub. No.: WO99/47910
PCT Pub. Date: Sep. 23, 1999

(30) Foreign Application Priority Data

Mar. 16, 1998 (DE) ......................... 198 11 395

(51) Int. Cl.⁷ .................. H01J 47/00; G01N 23/00
(52) U.S. Cl. ................. 250/305; 250/311; 250/310
(58) Field of Search ............... 250/310, 311, 250/307, 305

(56) References Cited

U.S. PATENT DOCUMENTS 5,578,823 A 11/1996 Taniguchi
5,713,364 A * 2/1998 DeBaryshe et al. .......... 128/664
5,798,524 A * 8/1998 Kundmann et al. ......... 250/305

FOREIGN PATENT DOCUMENTS

DE  195 46 780  6/1996
DE  198 08 768  9/1998
WO  99/01753   1/1999

OTHER PUBLICATIONS

H. Tenailleau et al. (1992), "A new background subtraction for low–energy EELS core edges", Journal of Microscopy, GB, Oxford, Jun. 1992, pp. 297–306.
IBM Corp. (1993), "Spectroscopy Signal Processing Technique", IBM Technical Disclosure Bulletin, Dec. 1985, vol. 28, pp. 2903–2904.
K.E. Gorlen et al (1984), "Computerized analytical electron microscope for elemental imaging", National Institutes of Health, Bethesda, MD, Feb. 1984, pp. 912–921.

* cited by examiner

Primary Examiner—John R. Lee
Assistant Examiner—Kalimah Fernandez
(74) Attorney, Agent, or Firm—Collard & Roe, P.C.

(57) ABSTRACT

The intention is to provide a process for the contrast enhancement of a specific particle in an image of a specimen, taken by a transmission electron microscope, in which a calculated contrast-rich image is created by way of the background intensities calculated from the intensities of a first image being drawn off pixel by pixel, whereby the background intensities are calculated as a function of the intensities of a second image. In this situation, it is intended that this process should feature a higher range of application than processes known hitherto, and, in particular, are well-suited for contrast enhancement for gold particles in immuno-gold marking. It is proposed, for this purpose, that the first image be taken under conditions in which the particle features the highest possible contrast, and that the second image is taken in a selected energy window which is selected in such a way that the contrast difference between the two images for the particle differs by the corresponding contrast difference for at least a second specimen constituent.

23 Claims, 5 Drawing Sheets

METHOD FOR ENHANCING THE CONTRAST FOR A TRANSMISSION ELECTRON MICROSCOPE

BACKGROUND OF THE INVENTION

The invention relates to a process for the contrast enhancement for a specific particle in an image of a specimen recorded by a transmission electron microscope.

One aspect of the present invention relates in particular to the high-resolution structure analysis by transmission electron microscopy in biological and medical research by means of immuno-gold marking. In this situation, gold grains of a size of between 1 nm and 20 nm are coupled to a specific biomolecule of the electron microscope specimen, with the result that this molecule can be indirectly demonstrated by means of the position of the gold grains in the specimen. It derives from this that gold, as a heavy metal, creates a particularly strong contrast and is therefore clearly visible.

However, the structure of the cell in which the gold-marked molecule is to be detected is likewise contrasted, in order, for example, to render individual cell compartments visible. This is done as a rile with uranium and/or lead. Because these elements are likewise heavy metals, they create a similar contrast to gold, so that the gold grains in many specimens cannot be unambiguously identified.

To facilitate the identification, larger gold grains can be used. With larger gold grains, however, the specificity of the coupling to the molecule is considerably reduced. It would also be possible to select a higher magnification, but this would still only show a relative small section of the cell, which is not always determinant alone. In addition, after the gold marking, it would be possible for silver to be deposited in a specific manner on the gold, so that the gold grains would be provided with a silver sheathing, and the contrast considerably increased. Such a silver depositing effect does not, however, occur with all gold grains, so that the contrast would not be uniformly distributed.

According to another formulation, it is possible for the contrast for a specific particle to be increased by image processing. In this case, a calculated contrast-rich image is created by calculated background intensities being derived pixel by pixel from the intensities of a first image, whereby the background intensities are calculated as a function of the intensities of a second image. In this situation the first image is recorded with an energy-filtering transmission electron microscope (EFTEM) in an energy window, in which an element-specific energy edge of the specific particle is located. The second image is recorded in an energy window which is located at energy values below the element-specific edge.

In an image-processing stage which follows this, a background intensity is determined as a linear representation of the intensities of the second image. The determination is effected in such a way that this function, which is dependent on the intensities of the second image in which none of the specific particles are present, is fitted to the intensities of the first image.

In view of the fact that in this manner the functional dependency of the background intensities of the first image was determined by the intensities of the second image, this background intensity is calculated for each pixel of the first image from the intensities of the second image, and subtracted from the intensity of the second image.

In this way a calculated image is acquired, in which the contrast for the specific particle is enhanced.

A process of this nature is disclosed, for example, in U.S. Pat. No. 5,578,823. In addition to this, H. TENAILLEAU ET AL. disclose in their article "A new background subtraction for low-energy EELS core edges", JOURNAL OF MICROSCOPY, GB, OXFORD, Vol. 166, No. 3, June 1992, pages 297 to 306, an improved extrapolation function, which can be applied in the process applied in U.S. Pat. No. 5,578,823, depending on the application instance.

A precondition for the performance of this process is that the specific particle features an element-specific energy loss edge, such as, for example, the energy loss edge of uranium at 120 eV or the energy loss edge of phosphorous at 160 eV.

However, not all particles feature a specific energy loss edge which delivers a signal which can in practice be selectively demonstrated. For example, gold does indeed feature two specific energy loss edges, a first at 60 eV and another at over 2000 eV. The first edge, at 60 eV, however, delivers a weak signal on a high non-element-specific background, with the result that this signal does not in practice allow for selective representation. The second edge, at over 2000 eV, is not detectable, since as early as about 1000 eV the inelastic signals become so weak that detection is virtually impossible any longer.

SUMMARY OF THE INVENTION

The objective on which the present invention is based is therefore of providing a contrast enhancement process of generic type, which features a broad range of application, and is not mandatorily related to the present of specific energy loss edges. In particular, the process should allow for a contrast enhancement for gold particles with immuno-gold marking.

As a solution, the invention proposes a contrast enhancement process of generic nature, in which the first image is taken under conditions in which the particle features the highest contrast possible, and in which the second image is taken in a selected energy window which is selected in such a way that the contrast difference between the two images differs for the particle by the corresponding contrast difference for at least one second specimen constituent.

This process for contrast enhancement according to the invention differs from the contrast enhancement process described heretofore by a fundamental difference in the properties of the images used for the image processing. With the contrast enhancement processes functioning according to the prior art, the images are selected in accordance with the specific energy loss edge of the element of which the contrast is to be enhanced. The first image is in this case recorded in an energy window which encloses the specific energy loss edge of the element. The second image is recorded in an energy window which lies below the specific energy loss edge.

With the images according to the contrast enhancement process according to the invention, a specific energy loss edge which may be present of the particle of which the contrast is to be enhanced does not play any part. This process is accordingly well-suited both for particles which do not feature any specific energy loss edge, as well as for particles of which the specific energy loss edge does not deliver selectively detectable signals. It has transpired in particular that this process is particularly well-suited for the contrast enhancement of gold.

With the contrast enhancement process according to the invention, the first image is recorded under conditions in which the particle features the highest possible contrast. This can, for example, be an image of the specimen with a transmission electron microscope without energy filter. It is likewise possible and, in particular, of advantage if the particle is a gold particle, for the first image to be taken in an energy window of 0 eV. With an energy-filtering transmission electron microscope, this means that the electrons are selected which have not lost any energy.

If the specimen contains yet another specimen constituent, in addition to the specific particle and the second specimen constituent, it can be of advantage if at least one further image is taken in another selected energy window, which is chosen in such a way that the contrast difference between the first and the further image and/or the second and the further image for the particle and/or for the second specimen constituent differs from the corresponding contrast difference for the further specimen constituent.

As a result, a set of images is prepared in which the second image and the further image in each case contain selective information about two specimen constituents.

In this way it is possible for the background intensities to be calculated as a function of the intensities of the second and the further image. In particular, the background intensities can be calculated as linear representations of the intensities of the second and further images.

Adequate results with minimum computer effort can already be achieved if the background intensities are represented as polynomials of the first or higher (1–3) degree by the intensities of the second and the further images. With such a representation, it is sufficient for an additive coefficient to be determined and a multiplicative coefficient for each of the intensities of the second and the further image.

To advantage, the background intensity function is derived by fitting to the intensities of the first image. If the background intensity function comprises a linear representation, then the corresponding coefficients can be determined by each known static fitting process.

It goes without saying that with a polynomial of the first degree, in which only three coefficients are to be determined, the time required for determining the background intensity function will be minimised.

The time required for this can be further reduced by the fitting being effected solely for selected pixels, arranged in a matrix. In particular, it is possible for every tenth pixel of every tenth pixel row to be used to determine the background intensity function. With a pixel matrix of 1024×1024 image pixels, some 10,000 image pixels are therefore derived, which are used to determine the background intensity function.

To this extent, the use of a pixel matrix for fitting the background intensity function is also inventive, independently of the other features of the contrast enhancement process according to the invention. It has been demonstrated that individual pixels of the pixel matrix which represent by chance one of the specific particles, for example gold, do not come into account with the fitting carried out.

Should it transpire, after the calculation of the contrast-rich image, that a contrast enhancement has been obtained which is inadequate, which may be due to excessive density of the specific particles (gold), those pixels selected and arranged in the matrix can be chosen which are located on an image of the specific particle. The background intensity function can then again be fitted to the intensities of the first image, whereby the pixels selected in this manner are not taken into account in the matrix, or are replaced by other pixels. This second step, too, in which the matrix is adapted if necessary to the special circumstances which pertain, can be carried out automatically, with the result that, as before, this process is suitable for automated particle evaluation.

It goes without saying that with further specimen constituents further images can be taken with appropriate energy windows and can be processed.

If a particle of the specimen features a specific energy loss edge, which delivers a selectively representable signal, it is to advantage for energy windows of the second image and/or a further image to be selected in such a way that the particle-specific energy edge of this specimen constituent, for preference an element-specific energy edge, is located in this window. This makes it possible for this specimen constituent to be detected in a particularly selective manner, and for the background intensity function to be determined precisely in this respect.

In this connection, it is to be pointed out that the present contrast enhancement process according to the invention in this case specifically makes use of the specific energy loss edge of another particle to enhance the contrast for the specific particle. No use is made of an energy loss edge which may be present of the specific particle.

If the specimen contains uranium, for example, it is of advantage if an image is taken at an energy window of 120 eV, the specific energy loss edge of uranium.

It is further possible for energy windows of the second image and/or a further image to be selected in such a way that the relative contrast of the particle in either this image or the first image features the same qualifying signs as a further specimen constituent, while the relative contrast of the particle in the other image in each case features a contrasting qualifying sign to the further specimen constituent.

In this situation, the term "relative contrast" designates the manner in which a particle stands out in a specific intensity from the background or the background intensity. Depending on the energy window selected, and depending in the particle, this may appear lighter or darker than the surroundings. To this extent, the term qualifying sign of the relative contrast relates to whether a particle is shown lighter or darker than the background.

The fact that a specific specimen constituent is shown in an image with another qualifying sign than the particle of which the contrast is to be enhanced, and is shown in another image with the same sign, allows for a relatively good selection of this specimen constituent, and therefore a correspondingly precise determination of the background intensity function.

Such a contrast property distinguishes heavy metals in particular, i.e. also gold, from other conventional specimen materials. Heavy metals accordingly appear darker at lower energy values than their surroundings. From a specific energy value, by contrast, they are shown as lighter.

Specifically, at about 60 eV gold grains appear darker than the surroundings, whereby at 0 eV they provide the strongest negative contrast. Above 70 eV gold grains are shown lighter.

In this context it has been shown to be of advantage if a further image is taken in an energy window of 40 eV.

Surprisingly, it has also transpired that with a uranium-contrasted and lead-contrasted specimen with immuno-gold marking, taken with images at 0 eV, 40 eV, and 120 eV, signals of both uranium and lead, as well as signals incurred by the thickness of the specimen, can be successfully filtered, and essentially the pure gold signal remains over.

Accordingly, it is also possible for the energy window of the second image and/or of a further image to be selected in such a way that the relative contrast of a second specimen constituent in either this image or the first image features the same qualifying sign as a further specimen constituent, while the relative contrast of the second specimen constituent in the other image in each case features a contrasting qualifying sign to the other specimen constituent.

BRIEF DESCRIPTION OF THE DRAWINGS

Further advantages, aims, and properties of the process according to the invention are explained hereinafter in the description of an embodiment and the appended drawing, which show:

FIG. 1a An image of a specimen with an energy window of 0 eV with an enlargement of M=4000, FIG. 1b An image of the specimen with an energy window of between 40 eV and 50 eV, FIG. 1c An image of the specimen with an energy window of between 115 eV and 125 eV, FIG. 2 Images of gold grains from the specimen according to FIG. 1 with high enlargement (M=31500) and different energy loss values, FIG. 3a A schematic example specimen in a sectional view, FIG. 3b A schematic representation of measured intensities in images of the example specimen according to FIG. 3a, FIG. 3c The gold signal calculated from the intensities according to FIG. 3b, FIG. 4 The gold distribution calculated from FIGS. 1a to 1c, and FIG. 5 The calculated gold distribution in superimposition with the 0 eV image according to FIG. 1a.

DETAILED DESCRIPTION

The embodiment comprises a specimen in which an ultra-thin layer of a cell with uranium and lead has been rendered visible, in which the DNA has been marked with gold grains of 6 nm.

Figure 1A:
Figure 1B:
Figure 1C:

Pictures are taken of the specimen with an energy-filtered transmission electron microscope, whereby electrons were selected which have not lost any energy (FIG. 1a), which have lost between 40 and 50 eV (FIG. 1b), and which have lost between 115 and 125 eV (FIG. 1c).

In this situation, the image at 0 eV was selected because it supplies the sharpest contrast for the gold grains. The window between 115 and 125 eV was selected because it is in this range that the element-specific energy loss edge of uranium is located, and uranium can accordingly be represented in an easily selective manner in this window.

Figure 2:
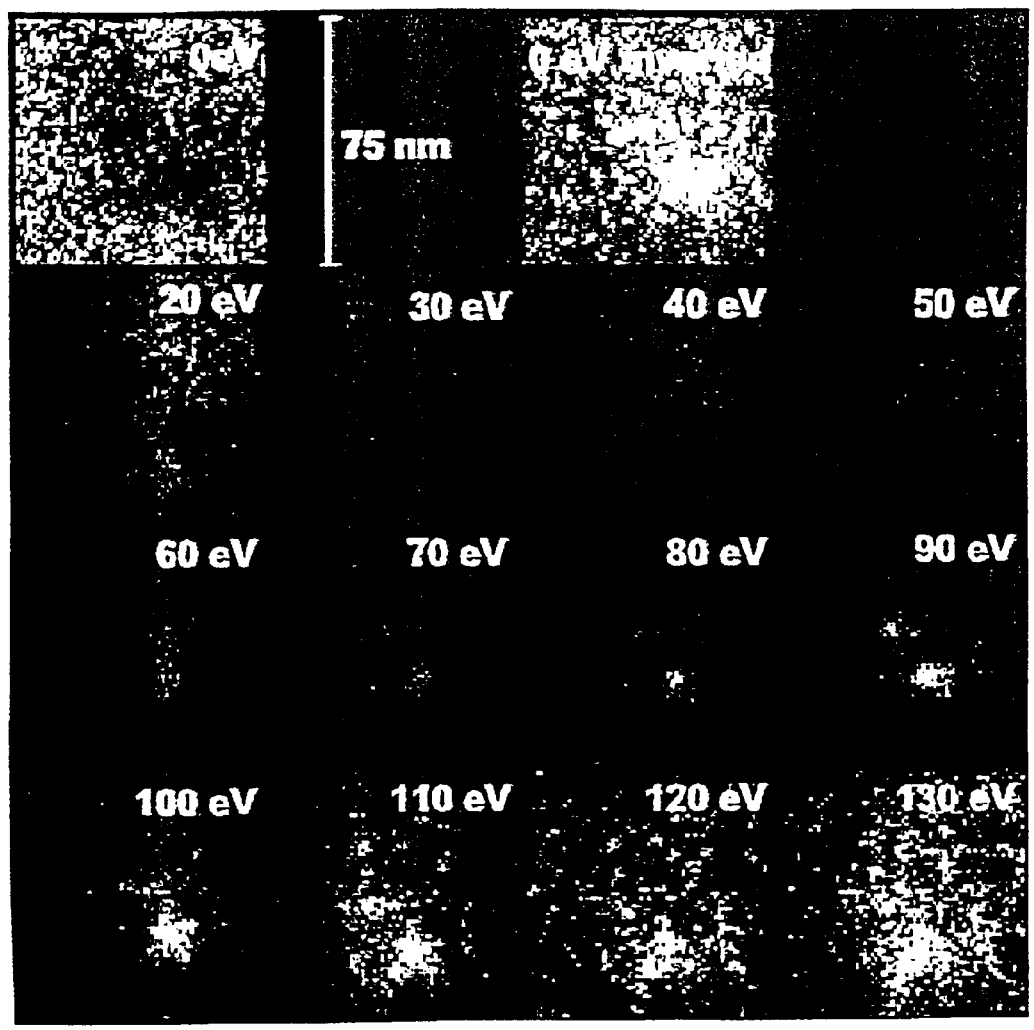

For the selection of the energy window between 40 and 50 eV, another contrast property of heavy metals was used, of gold in particular, which make it possible for the gold signal to be separated from the background. This property is shown in FIG. 2. In this case, gold grains from the specimen shown in FIGS. 1a to 1c were taken at high enlargement and at different energy loss values. As can be seen from FIG. 2, at about 50 ev the gold grains appear darker than the surroundings, whereby this provides the sharpest negative contrast at 0 eV. At between 70 and 120 eV the gold grains are shown lighter. From about 110 eV the gold grains can no longer be identified, since the signal is dominated by uranium.

In order to separate the contrast of the gold grains from the background, the intensity of the background $I_u$ is calculated as a linear function of the intensities at 45 eV ($I_{45}$) and at 120 eV ($I_{120}$).

$$I_u = c_0 + c_1 I_{45} + c_2 I_{120}$$

In order to calculate the intensity of the background, every tenth pixel of every tenth pixel row were selected from the 1,024×1,024 pixels of the images, and the function of the background intensities Iu for the approximately 10,000 pixels were then fitted to the intensities at 0 eV ($I_0$) in their coefficients $c_0$, $c_1$, and $c_2$.

Once the function of the background intensity had been determined in this way, the background intensity was derived for each pixel from the intensity at 0 eV:

$$I_{erg} = I_0 - I_u$$

so that essentially only the contrast caused by the gold remained over.

Figure 3A:
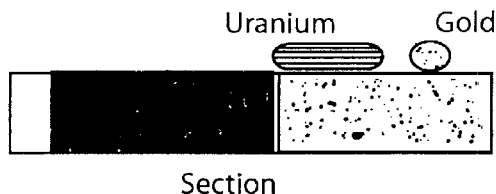
Figure 3B:
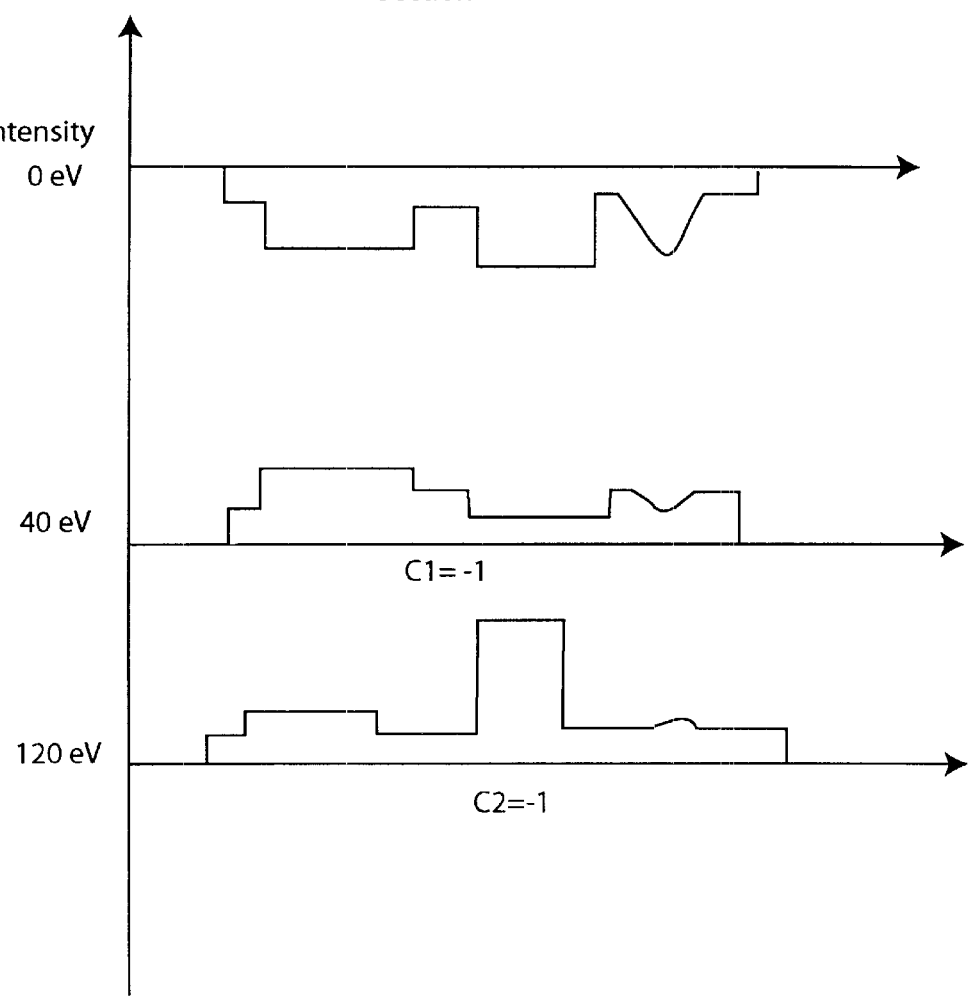
Figure 3C:
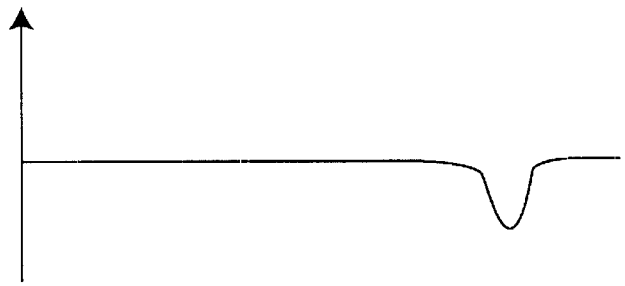

This is shown in schematic form in FIG. 3. The specimen consists of a section which does indeed have a uniform thickness, but of which the density varies. In this situation the dark grey represents a point of high density. In addition, a point with uranium and a gold grain is represented. Between the image at 0 eV and the images at 45 eV and 120 eV there is a contrast reversal for the specimen without heavy metals. The contrast for uranium in the 45 eV image is similar as for gold. The difference between gold and uranium is clear in the 120 eV image. While gold produces only a weakly positive contrast, the intensity for uranium is very much sharper. In this example, the constants $c_0=0$, $c_1=1$, and $c_2=1$ give the pure gold signal.

Figure 4:
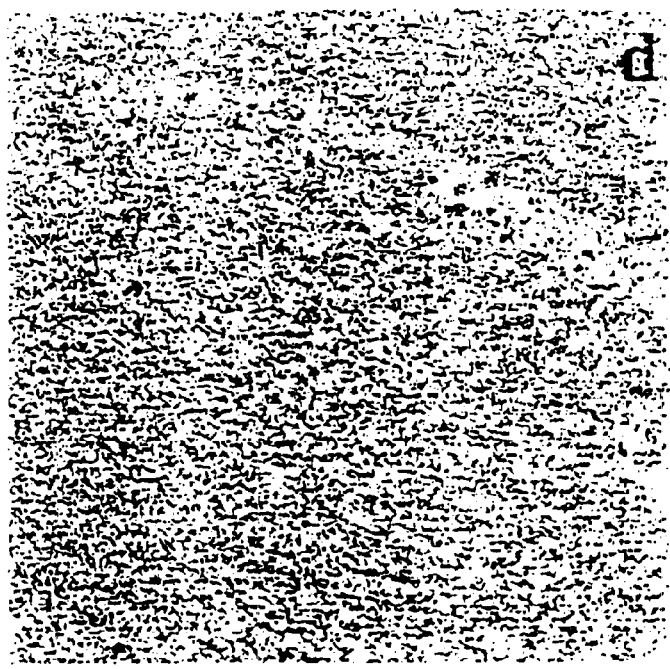
Figure 5:

The gold distribution calculated after the fitting for each pixel is represented as a binarised result image in FIG. 4, while FIG. 5 shows a superimposition of the intensities at 0 eV and the binarised result image.

With the process according to the invention, it is possible for the contrast of a gold-marked biomolecule (such as antibody, DNA or RNA probe) used for a localisation investigation to be optimised differentially and selectively. In this situation, a simultaneous consideration is possible of the uranium and/or lead contrast likewise present, which is essential for the structural recognition of the cell topology as a whole.

As the end result of the contrast optimisation, the contrast of the gold particle appears strongly emphasised, while the contrast of the cell structure is reduced in a defined manner, so that the position and number of the gold grains in relation to the underlying cell structure is unambiguously defined.

It is therefore possible with this process for an experiment in which a biomolecule was marked with gold to be evaluated more objectively and more reliably than hitherto. Thus, for example, the result image can be binarised and superimposed on the 0 eV image, so that more precise assessments are possible of the distribution of the molecule concerned within the cell. In addition to this, it is intended for it to be possible for these images to be evaluated, for example with computer support.

What is claimed is:

1. A process for enhancing a contrast of an image of a specimen, taken from a transmission electron microscope, said specimen comprising a specific particle and at least one second constituent, the process comprising the steps of:

taking a first image of said specimen wherein said specific particle has a highest possible contrast;

taking a second image in a selected energy window, wherein said energy window is selected such that a contrast difference between said first image and said second image of said particle differs from a corresponding contrast difference between said first image and said second image of said second specimen constituent; and creating a calculated contrast rich image by subtracting a set of calculated background intensities pixel by pixel from a set of intensities of said first image wherein said set of background intensities are calculated as a function of a set of intensities of said second image.

2. The contrast enhancement process as in claim 1, further comprising the step of taking at least one further image in a further selected energy window.

3. The process as in claim 2, wherein said further selected energy window is selected such that a contrast difference between said first image and said at least one further image of said particle differs from a corresponding contrast difference between said first image and said at least one further image of a further specimen constituent.

4. The process as in claim 2, wherein said further selected energy window is selected such that a contrast difference between said second image and said at least one further image of said particle differs from a corresponding contrast difference between said second image and said at least one further image of a further specimen constituent.

5. The process as in claim 2, wherein said further selected energy window is selected such that a contrast difference between said first image and said at least one further image of said second specimen constituent differs from a corresponding contrast difference between said first image and said at least one further image of a further specimen constituent.

6. The process as in claim 2, wherein said further selected energy window is selected such that a contrast difference between said second image and said at least one further image of said second specimen constituent differs from a corresponding contrast difference between said second image and said at least one further image of a further specimen constituent.

7. The contrast enhancement process as in claim 2, wherein said step of calculating said background intensities is based on said second image and said at least one further image.

8. The contrast enhancement process as in claim 7, wherein said step of calculating said background intensities includes calculating said background intensities as a linear representation of said second and said further image intensities.

9. The contrast enhancement process as in claim 8, wherein said step of calculating said background intensities includes representing said background intensities as a polynomial 1, or of a higher degree, by said second and said further image intensities.

10. The contrast enhancement process as in claim 1, further comprising a step of calculating said background intensities (IU) by fitting to said set of intensities of said first image.

11. The contrast enhancement process as in claim 10, wherein said step of fitting to said set of intensities of said first image includes fitting a plurality of selected pixels, whereby said plurality of selected pixels are arranged in a matrix.

12. The contrast enhancement process as in claim 11, further comprising the steps of choosing a pixel of said selected pixels that are located on an image of said specific particle after the creation of said contrast rich image; and comprising the step of evaluating said chosen pixel and repeating said fitting to said set of intensities of said first image, whereby said chosen pixel is not taken into account in said matrix or is replaced by another pixel.

13. The contrast enhancement process as in claim 1, wherein said energy window of said second image is selected such that in said first image a relative contrast of said particle has a same qualifying sign as a relative contrast of said second specimen constituent, and in said second image said relative contrast of said particle has an opposite qualifying sign as a relative contrast of said second specimen constituent.

14. The contrast enhancement process as in claim 1, wherein said energy window of said second image is selected such that in said first image a relative contrast of said particle has an opposite qualifying sign as a relative contrast of said second specimen constituent, and in said second image said relative contrast of said particle has a same qualifying sign as a relative contrast of said second specimen constituent.

15. The contrast enhancement process as in claim 2, wherein said energy window of said further image is selected such that in said first image a relative contrast of said particle has a same qualifying sign as a relative contrast of said further specimen constituent, and in said further image said relative contrast of said particle has an opposite qualifying sign as a relative contrast of said further specimen constituent.

16. The contrast enhancement process as in claim 2, wherein said energy window of said further image is selected such that in said first image a relative contrast of said particle has an opposite qualifying sign as a relative contrast of said further specimen constituent, and in said further image said relative contrast of said particle has a same qualifying sign as a relative contrast of said further specimen constituent.

17. The contrast enhancement process as in claim 2, wherein said energy window of said further image is selected such that in said first image a relative contrast of said second specimen constituent has a same qualifying sign as a relative contrast of said further specimen constituent, and in said further image said relative contrast of said second specimen constituent has an opposite qualifying sign as a relative contrast of said further specimen constituent.

18. The contrast enhancement process as in claim 2, wherein said energy window of said further image is selected such that in said first image a relative contrast of said second specimen constituent has an opposite qualifying sign as a relative contrast of said further specimen constituent, and in said further image said relative contrast of said second specimen constituent has a same qualifying sign as a relative contrast of said further specimen constituent.

19. The contrast enhancement process as in claim 1, wherein said specific particle is gold.

20. The contrast enhancement process as in claim 1, wherein said first image is taken in a window of 0 eV.

21. The contrast enhancement process as in claim 1, wherein said second image is taken in a window having an energy value of about 40 eV.

22. The contrast enhancement process as in claim 1, wherein said second image is taken in a window having an energy value of about 120 eV.

23. The contrast enhancement process as in claim 2, wherein one of said second or said further image is taken in a window having an energy value of about 40 eV, and the other one of said second or said further image is taken in a window having an energy value of about 120 eV.

* * * * *